(12) United States Patent
Olsson

(10) Patent No.: US 10,557,824 B1
(45) Date of Patent: Feb. 11, 2020

(54) RESILIENTLY DEFORMABLE MAGNETIC FIELD TRANSMITTER CORES FOR USE WITH UTILITY LOCATING DEVICES AND SYSTEMS

(71) Applicant: SeeScan, Inc., San Diego, CA (US)

(72) Inventor: Mark S. Olsson, La Jolla, CA (US)

(73) Assignee: SEESCAN, INC., San Diego, CA (US)

( * ) Notice: Subject to any disclaimer, the term of this patent is extended or adjusted under 35 U.S.C. 154(b) by 33 days.

(21) Appl. No.: 15/185,018

(22) Filed: Jun. 17, 2016

Related U.S. Application Data

(60) Provisional application No. 62/180,768, filed on Jun. 17, 2015.

(51) Int. Cl.
*G01N 27/82* (2006.01)

(52) U.S. Cl.
CPC .................................. *G01N 27/82* (2013.01)

(58) Field of Classification Search
None
See application file for complete search history.

(56) References Cited

U.S. PATENT DOCUMENTS

| | | | | |
|---|---|---|---|---|
| 3,747,036 A * | 7/1973 | Erdmann | ............... | G01R 33/02 324/234 |
| 3,932,872 A * | 1/1976 | Zenel | ............... | H01Q 7/08 174/102 R |
| 5,576,514 A * | 11/1996 | Fujimoto | ............... | H01B 7/0063 174/110 FC |
| 8,547,428 B1 * | 10/2013 | Olsson | ............... | G03B 37/005 348/374 |
| 2006/0006875 A1 * | 1/2006 | Olsson | ............... | G01V 3/081 324/338 |
| 2007/0018649 A1 * | 1/2007 | Prsha | ............... | G01V 3/088 324/326 |
| 2010/0208055 A1 * | 8/2010 | Olsson | ............... | H01B 7/182 348/84 |
| 2011/0239823 A1 * | 10/2011 | Narasimhan | ............... | B22F 1/02 75/246 |

OTHER PUBLICATIONS

Spring Steel Review, http://www.engineersedge.com/materials/spring-steel.htm, 2005.*
Metglas, http://www.rotima.ch/fileadmin/downloads/Amorphe_Materialien/2605-SA1_techn_bulletin.pdf, Jun. 25, 2013.*

* cited by examiner

*Primary Examiner* — Patrick Assouad
*Assistant Examiner* — Demetrius R Pretlow
(74) *Attorney, Agent, or Firm* — Steven C. Tietsworth, Esq.

(57) ABSTRACT

Flexible magnetic cores for generating magnetic fields in a utility locator system sonde are disclosed. The flexible core includes an elongate resiliently deformable rod and a flexible elongate structure of a high permeability ferromagnetic material disposed around the elongate resiliently deformable rod, with the resiliently deformable rod comprising fiberglass rod or similar resilient materials, and the flexible elongate structure comprising a plurality of bundles of wires of a high permeability/low loss ferromagnetic material.

21 Claims, 15 Drawing Sheets

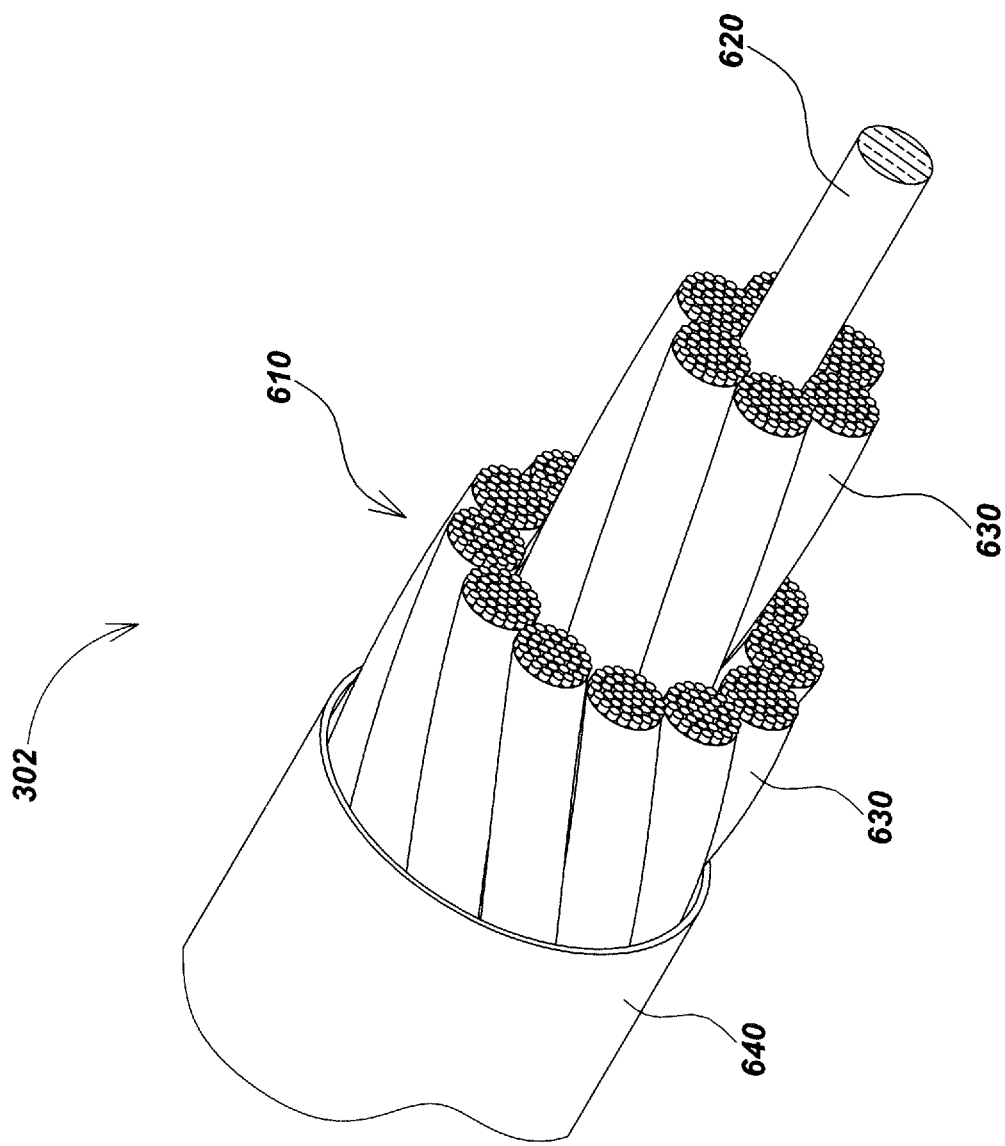

RESILIENTLY DEFORMABLE MAGNETIC FIELD TRANSMITTER CORES FOR USE WITH UTILITY LOCATING DEVICES AND SYSTEMS

CROSS-REFERENCE TO RELATED APPLICATIONS

This application claims priority under 35 U.S.C. § 119(e) to U.S. Provisional Patent Application Ser. No. 62/180,768, entitled RESILIENTLY DEFORMABLE MAGNETIC FIELD TRANSMITTER CORES FOR USE WITH UTILITY LOCATING DEVICES AND SYSTEMS, filed on Jun. 17, 2015, the content of which is incorporated by reference herein in its entirety for all purposes.

FIELD

This disclosure relates generally to flexible magnetic cores for use in electromagnetic field generating and transmitting devices. More specifically, but not exclusively, this disclosure relates to magnetic field sondes having magnetic cores of high magnetic permeability ferromagnetic ribbons, wires, or other elongate structures, and elongate resiliently deformable rods for use in hidden or buried utility locating devices and systems.

BACKGROUND

Devices for utility locating include transmitter antennas having magnetic cores of ferromagnetic material for use with coils, current sources, and/or other components generate and send magnetic field signals. One type of such device is known as a sonde or beacon. Sondes or beacons typically include a power supply, current signal source, and amplifier along with a dipole magnetic field antenna. Transmitted magnetic field signals may be continuous wave (CW) signals or, in some applications, may include encoded data or information or other signal modulation.

Signals from sondes, beacons, and similar devices may be used to transmit magnetic dipole fields at one or more frequencies and/or to send data to other utility locating system devices via transmitted magnetic field signals. Utility locators may be used to locate the sonde underground or within a cavity or opening by sensing the generated dipole magnetic field, typically at the ground surface. For example, a sonde deployed into an underground pipe on the end of a push-cable can generate a magnetic field signal that can be sensed by an above ground user with a utility locator, typically directly above the sonde's underground location. This application is a type of utility locating operation, also known as a "locate."

In related applications, a sonde may be combined with a video or still camera on the end of a push-cable, allowing the location of the camera under the ground to be determined in the locator, and the corresponding ground surface location (e.g., in latitude/longitude coordinates or other reference positions on the ground surface) to be associated and stored with an image or video captured within the pipe or cavity. Pipe characteristics or features, such as breaks, invasions of roots, corrosion, branches, etc. as shown in the images or video may then be precisely associated with surface positions or coordinates, and corresponding maps showing pipe features under the ground may be generated from collected data.

Antenna and magnetic cores known in the art for these applications typically rely only on a jacket wrapped about a core. The jacket provides a force to return the antenna to a straightened position after flexing, which is typically minimal. However, existing antennas and cores are limited in the amount of packing of ferromagnetic core material, as well as ability to flex and then self-straighten, thus reducing the overall effectiveness of the antenna. For example, limits in flexibility restrict the type of openings a sonde can be pushed through, and bends or obstructions in pipes may further limit sonde deployment. Moreover, when a core is bent, the magnetic field strength decreases, and if the core cannot readily self-straighten to return to its initial shape, the magnetic field signal strength may continue to be reduced until the core is returned to its non-flexed shape.

Accordingly, there is a need in the art to address the above-described as well as other problems.

SUMMARY

This disclosure relates generally to flexible magnetic cores for use in electromagnetic field generating and transmitting devices. More specifically, but not exclusively, this disclosure relates to magnetic field sondes having magnetic cores of high magnetic permeability ferromagnetic ribbons, wires, or other elongate structures, and elongate resiliently deformable rods for use in hidden or buried utility locating devices and systems.

For example, in one aspect, flexible magnetic cores and associated antennas and sondes in accordance with the disclosures herein may include a central resiliently deformable rod comprising fiberglass, carbon fiber, spring steel or other resilient materials that flex and then return readily to a straightened position after flexing without breakage or deformation. In some embodiments the cores may comprise a high tensile strength material to allow for tensile loading such as being pushed or pulled. The flexible core may include an elongate flexible structure of a high magnetic permeability/low loss ferromagnetic material such as a nickel-iron-molybdenum alloy (e.g., the alloy marketed under the trademark Carpenter HyMu 80® (also denoted herein for brevity as HyMu) or similar or equivalent alloys). In an exemplary embodiment the elongate flexible structure may comprise one or more layers or bundles of elongate ferromagnetic wires, ribbons, rods or other structures of the high magnetic permeability material. These may be helically wound around the resiliently deformable rod and may be covered by a jacket or housing in some embodiments.

In another aspect, a flexible magnetic field sonde may include a flexible magnetic core as described herein. The flexible core may be part of a dipole magnetic field sonde antenna.

In another aspect, a flexible duct fishing/tracing magnetic field sonde may include a flexible magnetic core as described herein.

In another aspect, a flexible magnetic field clamp for inducing signals onto a pipe or other conductor may include a flexible magnetic core as described herein.

In another aspect, various magnetic field generating and receiving devices may include a flexible magnetic core as described herein.

Various additional aspects, features, functions and details are further described below in conjunction with the appended Drawings.

BRIEF DESCRIPTION OF THE DRAWINGS

The present application may be more fully appreciated in connection with the following detailed description taken in conjunction with the accompanying drawings, wherein:

FIG. 6B is a segmented isometric view of the flexible magnetic core of the sonde embodiment of FIG. 4

DETAILED DESCRIPTION OF EMBODIMENTS

Overview

Figure 1:
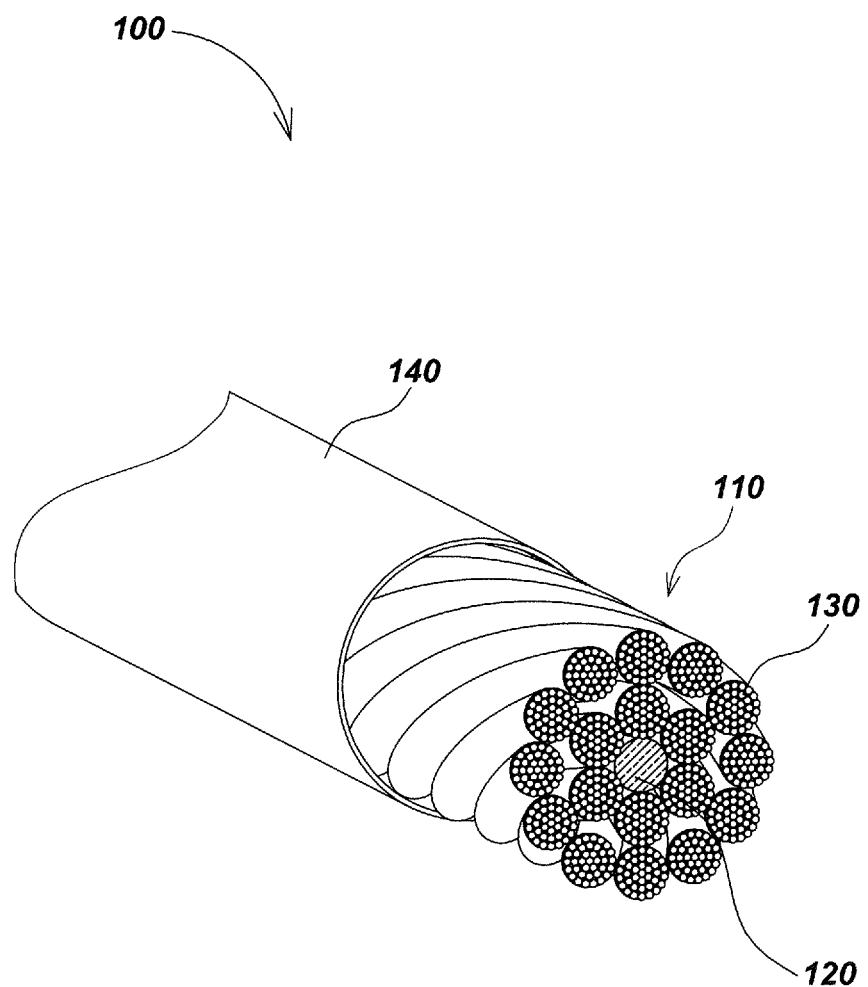
FIG. 1 is a partial isometric view of an embodiment of a flexible magnetic core in accordance with certain aspects.

Various aspects of magnetic cores, magnetic field antennas, utility locating systems, devices, and methods that may be used in various embodiments in conjunction with the details disclosed herein are described in co-assigned patents and patent applications including U.S. Pat. No. 5,808,239, issued Sep. 15, 1998, entitled VIDEO PUSH-CABLE; U.S. Pat. No. 5,939,679, issued Aug. 17, 1999, entitled VIDEO PUSH-CABLE; U.S. patent application Ser. No. 13/874,879, filed May 1, 2012, entitled HIGH BANDWIDTH PUSH-CABLES FOR VIDEO PIPE INSPECTION SYSTEMS; and U.S. patent application Ser. No. 14/207,517, filed Mar. 12, 2014, entitled HIGH BANDWIDTH PUSH-CABLES FOR VIDEO PIPE INSPECTION SYSTEMS.

Additional aspects of pipe inspection systems, apparatus, devices, configurations, and methods that may be used in various embodiments in conjunction with the details disclosed herein are described in co-assigned patents and patent applications including U.S. Pat. No. 7,009,399, issued Mar. 7, 2006, entitled OMNIDIRECTIONAL SONDE AND LINE LOCATOR; U.S. Pat. No. 7,221,136, issued May 22, 2007, entitled SONDES FOR LOCATING UNDERGROUND PIPES AND CONDUITS; U.S. Pat. No. 7,298,126, issued Nov. 20, 2007, entitled SONDES FOR LOCATING UNDERGROUND PIPES AND CONDUITS; U.S. Pat. No. 7,336,078, issued Feb. 26, 2008, entitled MULTI-SENSOR MAPPING OMNI-DIRECTIONAL SONDE AND LINE LOCATORS AND TRANSMITTER USED THEREWITH; U.S. Pat. No. 7,557,559, issued Jul. 7, 2009, entitled COMPACT LINE ILLUMINATOR FOR LOCATING BURIED PIPES AND CABLES; U.S. patent application Ser. No. 12/715,684, filed Mar. 2, 2010, entitled METHOD AND APPARATUS FOR HIGH-SPEED DATA TRANSFER EMPLOYING SELF-SYNCHRONIZINF QUADRATURE AMPLITUDE MODULATION (QAM); U.S. Pat. No. 7,863,885, issued Jan. 4, 2011, entitled SONDES FOR LOCATING UNDERGROUND PIPES AND CONDUITS; U.S. patent application Ser. No. 13/073,919, filed Mar. 28, 2011, entitled PIPE INSPECTION SYSTEM WITH JETTER PUSH-CABLE; U.S. patent application Ser. No. 13/346,668, filed Jan. 1, 2012, entitled PORTABLE CAMERA CONTROLLER PLATFORM FOR USE WITH PIPE INSPECTION SYSTEM; U.S. patent application Ser. No. 13/356,408, issued Jan. 23, 2012, entitled SONDES & METHODS FOR USE WITH BURIED LINE LOCATOR SYSTEMS; U.S. patent application Ser. No. 13/358,463, filed Jan. 25, 2012, entitled SELF-LEVELING INSPECTION SYSTEMS AND METHODS; U.S. patent application Ser. No. 13/532,721, filed Jun. 25, 2012, entitled MODULAR BATTERY PACK APPARATUS, SYSTEMS, AND METHODS; U.S. Pat. No. 8,106,660, issued Jan. 31, 2012, entitled SONDE ARRAY FOR USE WITH BURIED LINE LOCATOR; U.S. patent application Ser. No. 13/647,310, filed Oct. 8, 2012, entitled PIPE INSPECTION SYSTEM APPARATUS AND METHODS; U.S. Pat. No. 8,289,385, issued Oct. 16, 2012, entitled PUSH-CABLE FOR PIPE INSPECTION SYSTEM; U.S. patent application Ser. No. 13/769,202, filed Feb. 15, 2013, entitled SMART PAINT STICK DEVICES AND METHODS; U.S. patent application Ser. No. 13/774,351, filed Feb. 22, 2013, entitled DOCKABLE TRIPODAL CAMERA CONTROL UNIT; U.S. patent application Ser. No. 13/779,371, filed Feb. 27, 2013, entitled HORIZONTAL BORING INSPECTION DEVICE AND METHODS; U.S. Pat. No. 8,395,661, issued Mar. 12, 2013, entitled PIPE INSPECTION SYSTEM WITH SELECTIVE IMAGE CAPTURE; U.S. patent application Ser. No. 13/826,112, filed Mar. 14, 2013, entitled SYSTEMS AND METHODS INVOLVING A SMART CABLE STORAGE DRUM AND NETWORK NODE FOR TRANSMISSION OF DATA; U.S. patent application Ser. No. 13/941,381, filed Jul. 12, 2013, entitled SELF-GROUNDING TRANSMITTING PORTABLE CAMERA CONTROLLER FOR USE WITH PIPE INSPECTION SYSTEMS; U.S. patent application Ser. No. 14/027,027, filed Sep. 13, 2013, entitled SONDE DEVICES INCLUDING A SECTIONAL FERRITE CORE STRUCTURE; U.S. Pat. No. 8,540,429, issued Sep. 24, 2013, entitled SNAP ON PIPE GUIDE; U.S. Pat. No. 8,547,428, issued Oct. 1, 2013, entitled PIPE MAPPING SYSTEM; U.S. Pat. No. 8,587,648, issued Nov. 19, 2013, entitled SELF-LEVELING CAMERA HEAD; U.S. patent application Ser. No. 14/136,104, filed Dec. 20, 2013, entitled ROTATING CONTACT ASSEMBLIES FOR SELF-LEVELING CAMERA HEADS; U.S. patent application Ser. No. 14/148,649, filed Jan. 6, 2014, entitled MAPPING LOCATING SYSTEMS & METHODS; U.S. patent application Ser. No. 14/203,485, filed Mar. 10, 2014, entitled PIPE INSPECTION CABLE COUNTER AND OVERLAY MANAGEMENT SYSTEM; U.S. patent application Ser. No. 14/207,527, filed Mar. 12, 2014, entitled ROTATING CONTACT ASSEMBLIES FOR SELF-LEVELING CAMERA HEADS; U.S. patent application Ser. No. 14/210,291, filed Mar. 13, 2014, entitled OMNI-INDUCER TRANSMIT- TING DEVICES AND METHODS; U.S. patent application Ser. No. 14/215,290, filed Mar. 17, 2014, entitled SONDE DEVICES INCLUDING A SECTIONAL FERRITE CORE; U.S. patent application Ser. No. 14/216,358, filed Mar. 17, 2014, entitled SMART CABLE STORAGE DRUM AND NETWORK NODE SYSTEM AND METHODS; U.S. patent application Ser. No. 14/229,813, filed Mar. 28, 2014, entitled UTILITY LOCATOR TRANSMITTER APPARATUS & METHODS; U.S. patent application Ser. No. 14/271,255, filed May 6, 2014, entitled SPRING ASSEMBLIES WITH VARIABLE FLEXIBILITY FOR USE WITH PUSH-CABLES AND PIPE INSPECTION SYSTEMS; U.S. patent application Ser. No. 14/332,268, filed Jul. 15, 2014, entitled UTILITY LOCATOR TRANSMITTER DEVICES, SYSTEMS, AND METHODS WITH DOCKABLE APPARATUS; U.S. patent application Ser. No. 14/446,279, filed Jul. 29, 2014, entitled INDUCTIVE CLAMP DEVICES, SYSTEMS, AND METHODS; U.S. patent application Ser. No. 14/469,536, filed Aug. 26, 2014, entitled CABLE STORAGE DRUM WITH MOVABLE CCU DOCKING APPARATUS; U.S. patent application Ser. No. 14/516,558, filed Oct. 16, 2014, entitled ELECTRONIC MARKER DEVICES AND SYSTEMS; U.S. Pat. No. 8,908,027, issued Dec. 9, 2014, entitled ASYMMETRIC DRAG FORCE BEARING FOR USE WITH PUSH-CABLE STORAGE DRUM; U.S. patent application Ser. No. 14/642,596, filed Mar. 9, 2015, entitled PIPE CLEARING CABLES AND APPARATUS; U.S. Pat. No. 8,984,698, issued Mar. 24, 2015, entitled LIGHT WEIGHT SEWER CABLE; U.S. patent application Ser. No. 14/690,285, filed Apr. 17, 2015, entitled PIPE INSPECTION SYSTEM WITH PUSH-CABLE, JETTER, AND CAMERA HEAD; U.S. Pat. No. 9,041,794, issued May 26, 2015, entitled PIPE MAPPING SYSTEMS AND METHODS; U.S. patent application Ser. No. 14/798,177, filed Jul. 13, 2015, entitled MARKING PAINT APPLICATOR FOR USE WITH PORTABLE UTILITY LOCATOR; U.S. Pat. No. 9,080,992, issued Jul. 14, 2015, entitled ADJUSTABLE VARIABLE RESOLUTION INSPECTION SYSTEMS AND METHODS; U.S. patent application Ser. No. 14/800,490, filed Jul. 15, 2015, entitled UTILITY LOCATOR DEVICES, SYSTEMS, AND METHODS WITH SATELLITE AND MAGNETIC FIELD SONDE ANTENNA SYSTEMS; U.S. Pat. No. 9,085,007, issued Jul. 21, 2015, entitled MARKING PAINT APPLICATOR FOR PORTABLE LOCATOR; U.S. patent application Ser. No. 14/846,623, filed Sep. 4, 2015, entitled PIPE INSPECTION SYSTEM CAMERA HEADS; U.S. Pat. No. 9,134,255, issued Sep. 15, 2015, entitled PIPE INSPECTION SYSTEM WITH SELECTIVE IMAGE CAPTURE; U.S. patent application Ser. No. 14/935,878, filed Nov. 9, 2015, entitled INSPECTION CAMERA DEVICES AND METHODS WITH SELECTIVELY ILLUMINATED MULTISENSOR IMAGING; U.S. patent application Ser. No. 14/961,754, filed Dec. 7, 2015, entitled PORTABLE PIPE INSPECTION SYSTEMS AND APPARATUS; U.S. Pat. No. 9,207,350, issued Dec. 8, 2015, entitled BURIED OBJECT LOCATOR APPARATUS WITH SAFETY LIGHTING ARRAY; U.S. patent application Ser. No. 14/970,362, filed Dec. 15, 2015, entitled COAXIAL VIDEO PUSH-CABLES FOR USE IN INSPECTION SYSTEMS; and U.S. Pat. No. 9,277,105, issued Mar. 1, 2016, entitled SELF-LEVELING CAMERA HEAD. The content of each of the above-listed patents and patent applications are incorporated by reference herein in its entirety. The previously listed patents may be referred to collectively herein as the "incorporate applications" for brevity.

In typical applications, a flexible sonde in accordance with various aspects herein is coupled to a push-cable at one end and a camera head at another end. The camera head typically includes one or more imaging sensors and associated electronics, optical elements such as lenses, mechanical support elements, housings, optionally lighting elements such as LEDs or other light-emitting devices, and other elements such as software, firmware, housings and other structural elements, and the like for imaging areas being inspected and generating output still images or video streams. The camera is typically deployed by being pushed by an operator or, in some systems, a motor, into a pipe or other cavity. The camera may be pulled or drawn back to return it and the push cable to a cable storage reel, either by hand or mechanically. Operation of the camera is typically controlled by a device known as a camera control unit (CCU) or other devices with electronics and software for controlling camera operation and receiving images or video from the camera. Images or video may be displayed on a display element of the CCU or may be stored or transmitted via wired or wireless connections to other inspection system devices or systems. In some embodiments the CCU may be wirelessly coupled to a tablet, cellular phone, notebook computer, or other display device to allow the device to control camera operation and/or receive, display, and/or store images or video.

In a flexible sonde, it is desirable that a flexible magnetic core and associated elements bend and flex as the camera is forced through turns and bends within the pipe or other cavity, and then return to an initial straightened position after the bend is navigated. It may also be desirable to provide resilience in the core so that the sonde can bend and then be returned to its original straightened shape upon release of the flexing forces. It may also be desirable to maximize the packing of magnetic material within the core so as to maximize the corresponding radiated magnetic fields. In other embodiments beyond sondes, flexible cores may be used in devices such as clamps or duct tracing beacons, preferably with one or more of the above-described characteristics.

As noted previously, this disclosure relates generally to flexible magnetic cores for use in transmitting or receiving magnetic field signals, as well as devices and systems using such flexible cores. For example, in one aspect, this disclosure relates to magnetic field transmitters or sondes having magnetic cores of high magnetic permeability ferromagnetic ribbons, wires or other elongate structures and elongate resiliently deformable rods that may be used in various hidden or buried utility locating devices and systems as well as other magnetic field devices.

In another aspect, flexible magnetic cores and associated antennas and sondes may include a central resiliently deformable rod comprising fiberglass, carbon fiber, spring steel or other resilient materials that flex and then return readily to a straightened position after flexing without breakage or deformation. In some embodiments the cores may comprise a high tensile strength material to allow for tensile loading such as being pushed or pulled. The flexible core may include an elongate flexible structure of a high magnetic permeability/low loss ferromagnetic material such as a nickel-iron-molybdenum alloy (e.g., the alloy marketed under the trademark Carpenter HyMu 80® (also denoted herein for brevity as HyMu) or similar or equivalent alloys). In an exemplary embodiment the elongate flexible structure may comprise one or more layers or bundles of elongate ferromagnetic wires, ribbons, rods or other structures of the high magnetic permeability material. These may be helically wound around the resiliently deformable rod and may be covered by a jacket or housing in some embodiments.

In another aspect, a flexible magnetic field sonde may include a flexible magnetic core as described herein. The flexible core may be part of a dipole magnetic field sonde antenna.

In another aspect, a flexible duct fishing/tracing magnetic field sonde may include a flexible magnetic core as described herein.

In another aspect, a flexible magnetic field clamp for inducing signals onto a pipe or other conductor may include a flexible magnetic core as described herein.

In another aspect, various magnetic field generating and receiving devices may include a flexible magnetic core as described herein.

Various additional aspects, features, functions, and details are further described below in conjunction with the appended Drawings.

The terms "resilient" and "resiliently deformable" are used herein to refer to materials or structures that are able to flex or bend from a starting position and then return or spring back to the starting position without being permanently deformed or broken. In a typical application, it will be desirable that the flexible core can bend or flex by 45 degrees or more without damage or deformation. In some embodiments higher degrees of bending (e.g., up to 90 degrees or more) may be desirable, depending on the diameter and bend radius of the pipe or cavity being inspected.

The term "exemplary" is used herein to mean "serving as an example, instance, or illustration." Any aspect and/or embodiment described herein as "exemplary" is not necessarily to be construed as preferred or advantageous over other aspects and/or embodiments.

Example Flexible Magnetic Core Embodiments

Flexible magnetic core assemblies may include one or more elongate resiliently deformable rods or other elongate resiliently deformable elements along with an elongate high magnetic permeability/low loss ferromagnetic material in a flexible structure. The flexible elongate ferromagnetic material structure may be in a variety of shapes; however, in an exemplary embodiment the ferromagnetic material comprises wires which may be grouped into wire bundles. The wires and/or bundles may be helically wound and may be disposed around the one or more resiliently deformable rods or cores. In an exemplary embodiment a single resiliently deformable rod is positioned in the center of the core with wires or wire bundles around it; however, other elements and configurations may be used in alternate embodiments. The flexible core may further include an optional jacket or flexible housing or support structure. Flexible magnetic antenna embodiments may include a flexible core and associated wire coils disposed around the core and may be disposed in a flexible housing or support structure. The wire coils may be coupled to a current output source such as from an electronic driver circuit, with current flow in the coils around the core generating magnetic dipole fields.

In an exemplary embodiment, one or more resiliently deformable rods of fiberglass, carbon fiber, spring steel, or other flexible resilient material(s) may be disposed in the core assembly. In embodiments having a single resiliently deformable rod, the resilient rod may be placed at or near the center of the core assembly when viewed in cross-section. The elongate resilient rod(s) may further comprise a material having high-tensile strength for allowing the core to be pushed or pulled in some embodiments without breaking from axial loading.

Around the elongate resiliently deformable rod(s) within the flexible core, an elongate ferromagnetic structure of high magnetic permeability/low loss material may be disposed. For example, the ferromagnetic structure may comprise one or more layers or bundles of ferromagnetic ribbons, wires or other ferromagnetic elements (e.g., bars, films, weaves, coatings, jointed rigid elements, etc.). The ferromagnetic wires may be wound or formed, such as in a helical coil or other structure, around a single central resiliently deformable rod (in embodiments having a single rod) or around or interspersed with multiple resiliently deformable rods. In embodiments having more than one resilient rod, the rods may be disposed throughout the core assembly and may be interspersed with the ferromagnetic structural elements or weaved around the ferromagnetic structural elements (e.g., resilient rods interspersed with ferromagnetic wire bundles when viewed in cross-section). Small diameter spring steel bars or rod, music wire, piano wire, carbon fiber, beryllium copper, titanium, and other flexible resilient materials may also be used in various embodiments. In an exemplary embodiment with a single resiliently deformable rod and multiple wire bundles, the diameter of the rod and wire bundles may be approximately the same so as to maximize packing of high permeability magnetic material within the core. In addition to high magnetic permeability, low saturation of the ferromagnetic material is a desirable property, and the ferromagnetic material may be selected so as to optimize the magnetic properties at specific targeted operating frequencies of the sonde. For example, typical sonde operating frequencies for utility locating applications are in the range of 1 kHz to 1 MHz, however, some applications may operate down to frequencies as low as 100 Hz and as high as several MHz. Therefore, magnetic properties of high permeability and low loss may be selected to be optimized for specifically targeted operating frequencies.

Turning to the drawings, FIG. 1 illustrates details of portions of an exemplary embodiment of a flexible magnetic core 100 in cross-section in accordance with certain aspects. An example embodiment of use of a core such as core 100 is further illustrated in FIG. 4 as element 302 (and described subsequently herein in conjunction with FIG. 3).

Core embodiment 100 provides a substantial amount of high permeability/low loss ferromagnetic material packing within the cylindrical volume by using ferromagnetic wires in wire bundles helically wrapped a central resilient core. This configuration provides resiliency to allow the core to bend and flex significantly but then return to its original shape without permanent deformation or breakage.

As shown in FIG. 1, flexible magnetic core embodiment 100 includes a core assembly 110 comprising an elongate resiliently deformable element 120, disposed within an elongate high magnetic permeability/low loss structure, such as the plurality of wires in wire bundles 130. The central resilient rod 120 may comprise fiberglass, carbon fiber, spring steel, or other material(s) having resiliency. Although the core is not generally subject to stretching or axial breakage loading, in some embodiments high tensile strength may be desirable if the core is used in an application where it is pulled or otherwise subjected to axial loading. The wires within bundles 130 may comprise any of the various high permeability/low loss materials disclosed herein or other similar or equivalent materials.

In some embodiments (not illustrated), multiple central resilient rods may be included in the core, optionally with other flexible or structural elements, to provide straightening force to the core. In an exemplary embodiment as shown in FIG. 1, the high magnetic permeability layer comprises a plurality of wire bundles 130. Each wire bundle 130 may comprise strands of HyMu 80 (i.e., un-oriented 80% nickel-iron-molybdenum alloy) and/or other high magnetic permeability/low loss material(s) (e.g., having permeability on the order of 5,000 Mu or higher)).

In the exemplary embodiment shown in FIG. 1, the strands may be helically arranged within each wire bundle 130; however, they may be arranged axially in alternate embodiments or in other structures, such as by being weaved or braided, etc. The wire bundles 130 may further be wound about central resilient rod 120, such as in an additional helical winding, to form the flexible elongate high permeability structure. In other embodiments (not illustrated), additional numbers or rows of wires and/or wire bundles, or other structures such as high magnetic permeability bars, sheets, ribbons, jointed rigid segments, etc. may be arranged or wound/weaved in various other patterns in various additional flexible magnetic antenna embodiments.

A jacket 140 may optionally encapsulate the core assembly 110. The jacket may be of an airtight or watertight plastic or other protective material and/or may otherwise provide protection to the internal elements of the antenna from the external environment either alone or in conjunction with additional layers. The jacket 140 is shown in FIG. 1 partially removed from the core assembly 110 for the purpose of illustration; however, in a typical implementation it would be closed and sealed.

Figure 2:
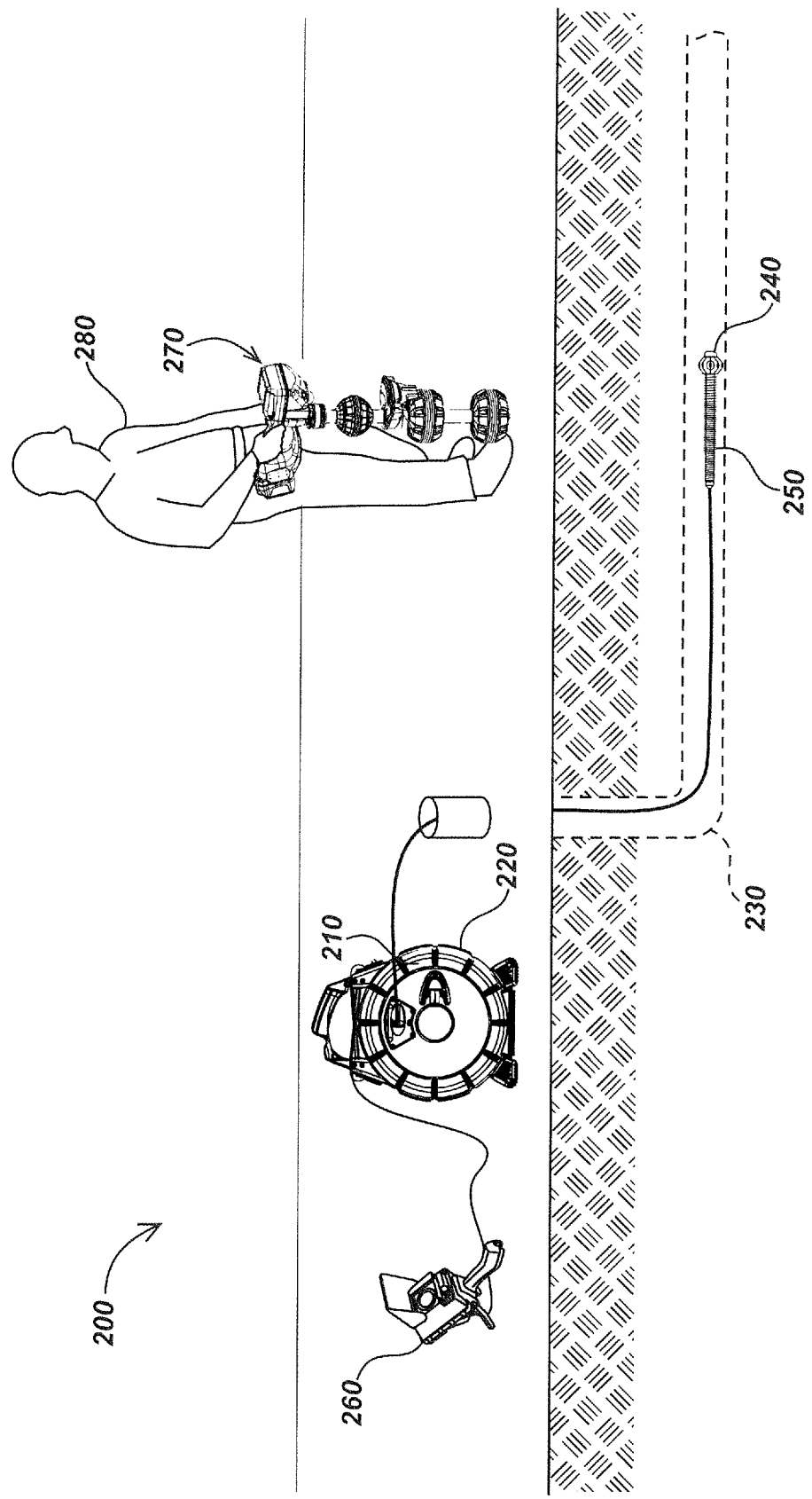
FIG. 2 is an exemplary utility locating and pipe inspection system including a magnetic field sonde embodiment with a flexible magnetic core.

Turning to FIG. 2, an exemplary embodiment 200 of a utility locating and pipe inspection system is shown. System 200 may include a push-cable 210 that may be removably stored on a push-cable drum reel 220 and pushed or otherwise deployed into a pipe 230. An electrical or optical connection may be provided by the push-cable between the drum reel 220 (and associated camera control unit (CCU) 260) and a camera head 240 disposed on or about a distal end of push-cable 210 so that the images or video may be stored or displayed on the CCU or transmitted via wired or wireless connection from the CCU to another device (not shown) such as a tablet, cellular phone, remote computing system, and the like. A proximal end of the push-cable 230 may be operatively coupled to the storage drum 220 and/or to the CCU 260. Images or video may be provided from the camera head 240 through electrical or optical conductors in the push-cable 230 to the drum 220 and CCU 260.

A coil spring 250 may be disposed around a segment of push-cable 210 behind camera head 240 for additional protection and rigidity as the camera head 240, coil spring 250 and push-cable 210 are forced into the pipe 230 (and through any bends and turns within). The camera head 240 may be configured to generate inspection data signal(s) corresponding to video and/or still images and/or other inspection data from within pipe 230. The inspection data signals may be communicated to a video display device such as the camera control unit (CCU) 260 connected to the drum reel 220 and may be rendered on an display element, such as an LCD or other panel, on the CCU.

Control signals may be generated by CCU 260 and/or other system device(s) configured to control various operations of the camera head 240 as well as drum reel 220 and/or other wired or wirelessly connected system devices (not illustrated). The push-cable 210 may communicate control signals as well as inspection data signal(s) between camera head 240 and drum reel 220, as well as transmit electrical power to camera head 240 from a power source, such as one or more batteries (not illustrated), an AC driven power supply (not illustrated) or other power sources on or coupled to CCU 260 and/or drum reel 220.

A utility locator 270, as held by a user 280, may determine, track, and/or map the location of the push-cable 210 within pipe 230 and determine a position of the camera head 240 on the ground surface from magnetic field signals provided by an associated sonde (not shown in FIG. 2 but typically integral with or coupled to the camera head or push-cable). Further details regarding embodiments of utility locating and/or pipe inspection devices, systems, and methods as may be used in additional embodiments in conjunction with the disclosures here are described in the various incorporated patents and patent applications.

Figure 3:
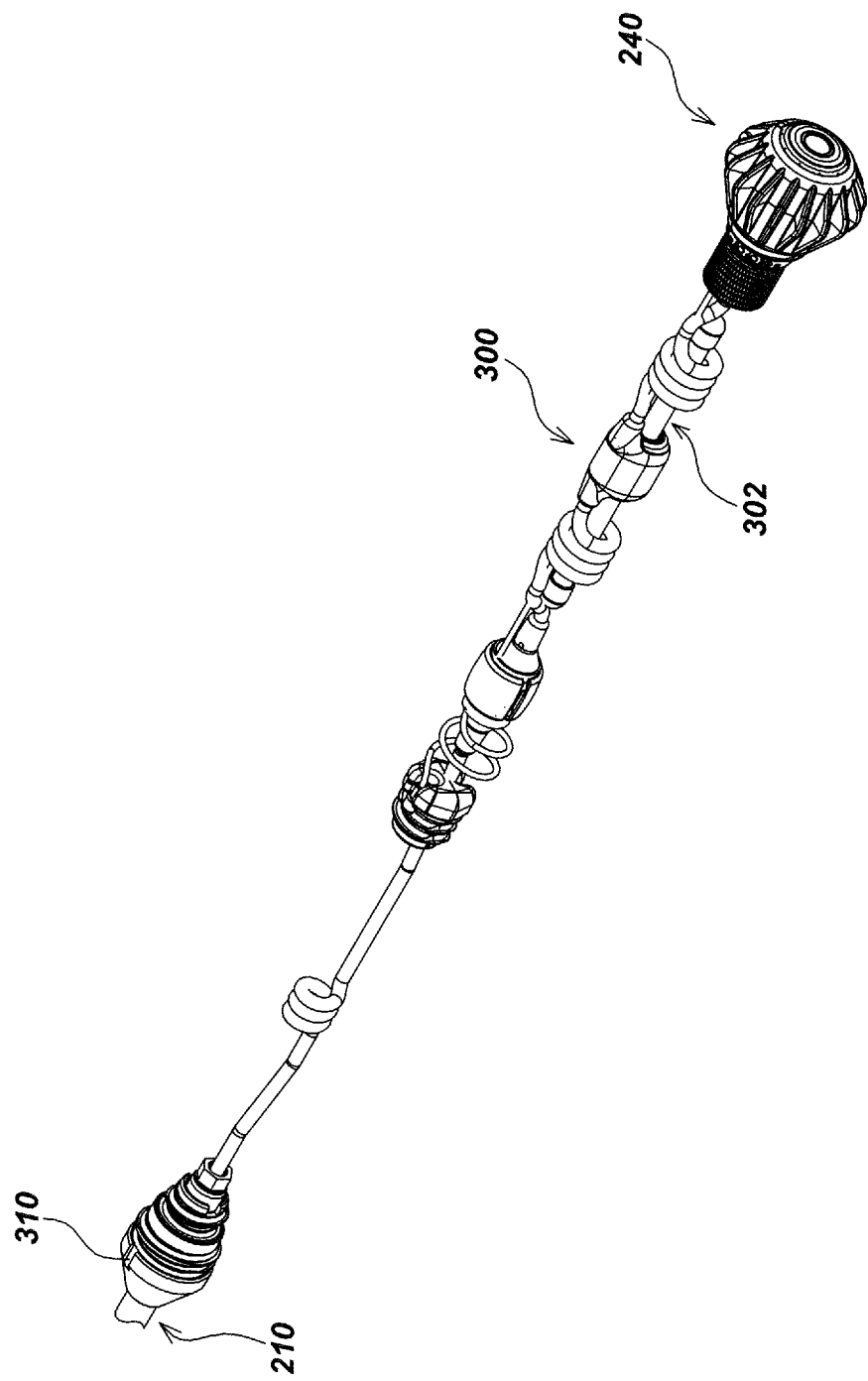
FIG. 3 is an isometric view of a flexible sonde embodiment with a flexible magnetic core embodiment connected to a push-cable on one end and a camera head on the other end.

As shown in FIG. 3, a flexible sonde embodiment 300, including a flexible magnetic core 302 which may correspond with the core 100 of FIG. 1, may be disposed between push-cable 210 and camera head 240. This configuration may be used to minimize the cross-sectional area of the joint between the push-cable and camera head; however, in alternate embodiments the sonde may be disposed within the camera head and/or push-cable or coupled to these elements or other inspection systems elements instead. The flexible sonde embodiment 300 of FIG. 3 may be positioned within coil spring 250 as shown in FIG. 2 to minimize the overall cross section and protect the sonde during deployment through turns in the pipe or from pipe obstructions or defects such as breaks (with FIG. 3 showing the distal end of the push-cable 210 of FIG. 2 with the spring 250 removed for clarity).

The flexible sonde 300 generates magnetic field signals (typically in a magnetic field dipole pattern) that may be detected at the ground surface with a locator device, such as the locator device 270 of FIG. 2. Detection of the magnetic field signal may be used for locating, tracking, and/or mapping the location of the flexible sonde 300 beneath the ground. This may be used to associate captured images and/or video collected via camera head 240 (FIG. 2) with the locator information determined by locator 270. The locator information may be stored with the captured images and/or video in a non-transitory computer-readable memory or other non-transitory storage device. For example, the associated images/video and position data may be stored in the locator, the CCU, or in other local or remote system devices such as tablets, cellular phones, or remote server systems.

Additional details of various embodiments of flexible sondes are disclosed in co-assigned U.S. Pat. No. 7,221,136, issued May 22, 2007, entitled SONDES FOR LOCATING UNDERGROUND PIPES AND CONDUITS and U.S. Pat. No. 7,863,885, issued Jan. 4, 2011, entitled SONDES FOR LOCATING UNDERGROUND PIPES AND CONDUITS.

Figure 4:
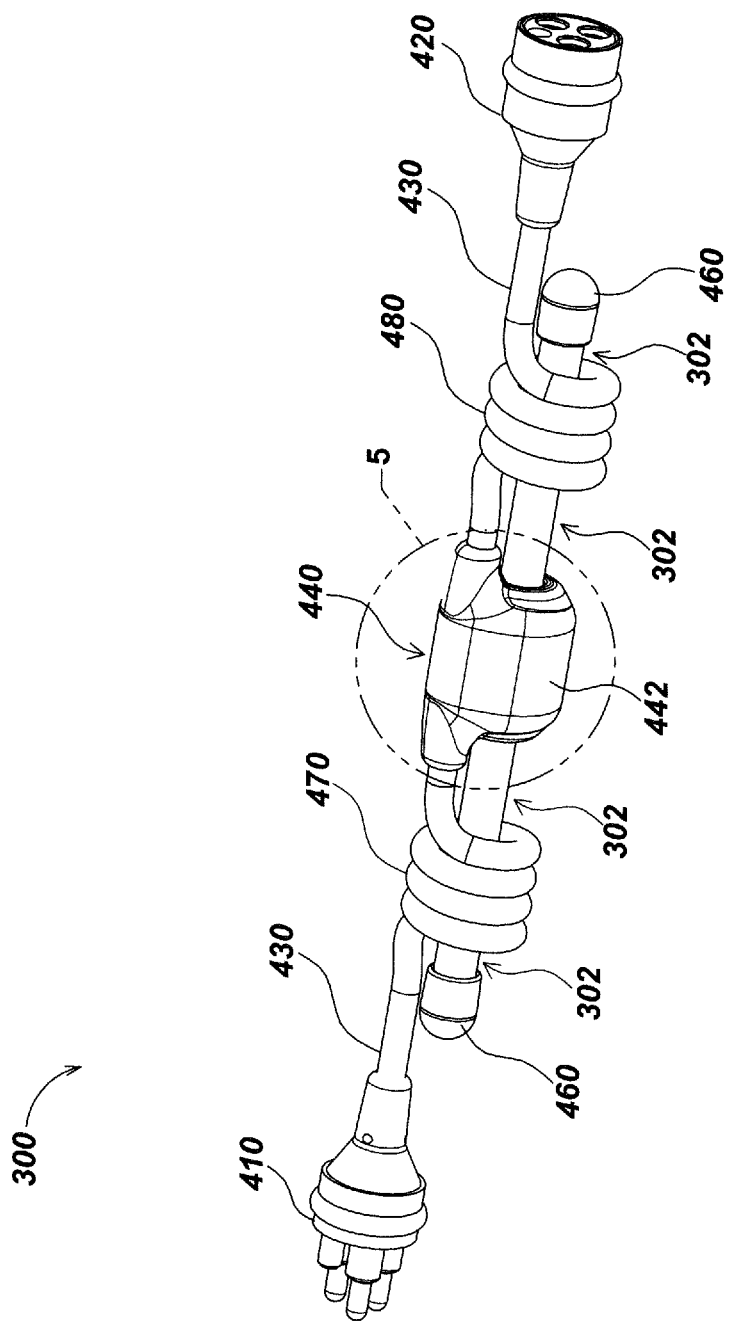
FIG. 4 is a detailed isometric view of the sonde embodiment of FIG. 3.

Turning to FIG. 4, additional details of flexible sonde embodiment 300 are illustrated. As shown in FIG. 4, sonde 300 may include a rear connector 410 that may operatively connect to push-cable 210 via termination 310, and a front connector 420 that may operatively connect to the camera head 240 (both as shown in FIG. 3) along with associated conductors to allow signals between the push-cable and camera head pass through the sonde. Cable 430 may be disposed between the rear connector 410 and front connector 420 to communicate data and providing electrical power to the camera head 240 and coil and electronics assembly 440. Coil and electronics assembly 440 may be used to induce electromagnetic signal onto flexible magnetic core assembly 302 protruding about each end of the coil and electronics assembly 440. End caps 460 may seat and may optionally be adhered to either end of flexible magnetic core assembly 302 providing a watertight seal. The cable 430 may further include coiled segments 470 and 480 that may wrap about the flexible magnetic core assembly 302 and accommodate slack in the cable 430. The coil and electronics assembly 440 may externally include a waterproof housing 442 providing protection from the external environment to components housed within.

Figure 5:
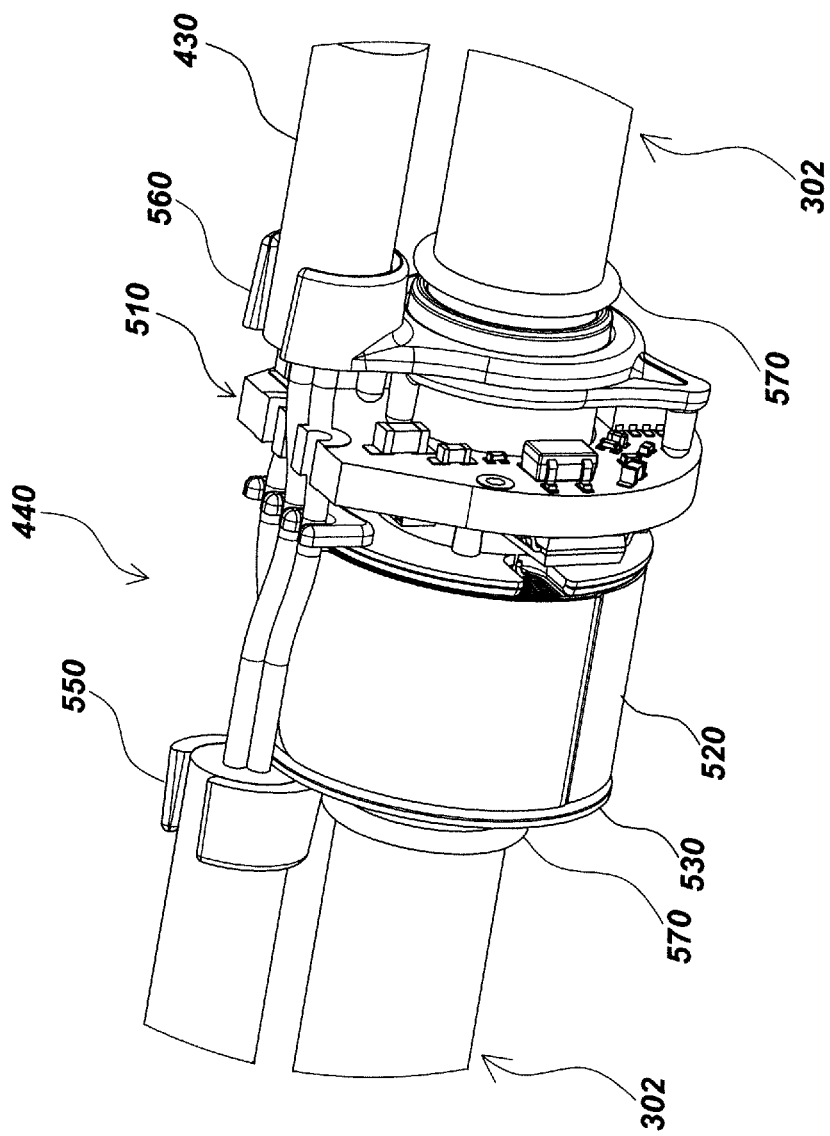
FIG. 5 is a detailed interior view of a coil and electronics assembly from the sonde embodiment of FIG. 4.

The coil and electronics assembly 440, as illustrated in FIG. 5 with housing 442 (FIG. 4) removed, may include a PCB 510, a coil 520 composed of multiple turns of wire further secured to a bobbin 530 seated centrally about a segment of the flexible magnetic core assembly 302. PCB 510 may contain electronic circuitry for supplying coil 520 with an oscillating electric signal that may induce the flexible magnetic core assembly 302 to emit magnetic field signal(s) at a predetermined frequency that may be remotely detected using, for instance, a locator device such as the locator device 270 of FIG. 2. The magnetic field signal may be continuous wave (CW) or, in some embodiments, may include encoded data modulated on the magnetic field signal.

The coil and electronics assembly 440 may further include a rear clip 550 and a front clip 560 to further secure the PCB 510, bobbin 530, coil 520, and flexible magnetic core assembly 302 to cable 430. A series of O-rings 570 may be positioned within the housing 442 (as shown in FIG. 4) about each end (through which the flexible magnetic core assembly 302 may protrude). The O-rings 570 may be seated circumferentially about the flexible magnetic core assembly 302, providing a watertight seal between the housing 442 and the flexible magnetic core assembly 302.

Figure 6A:
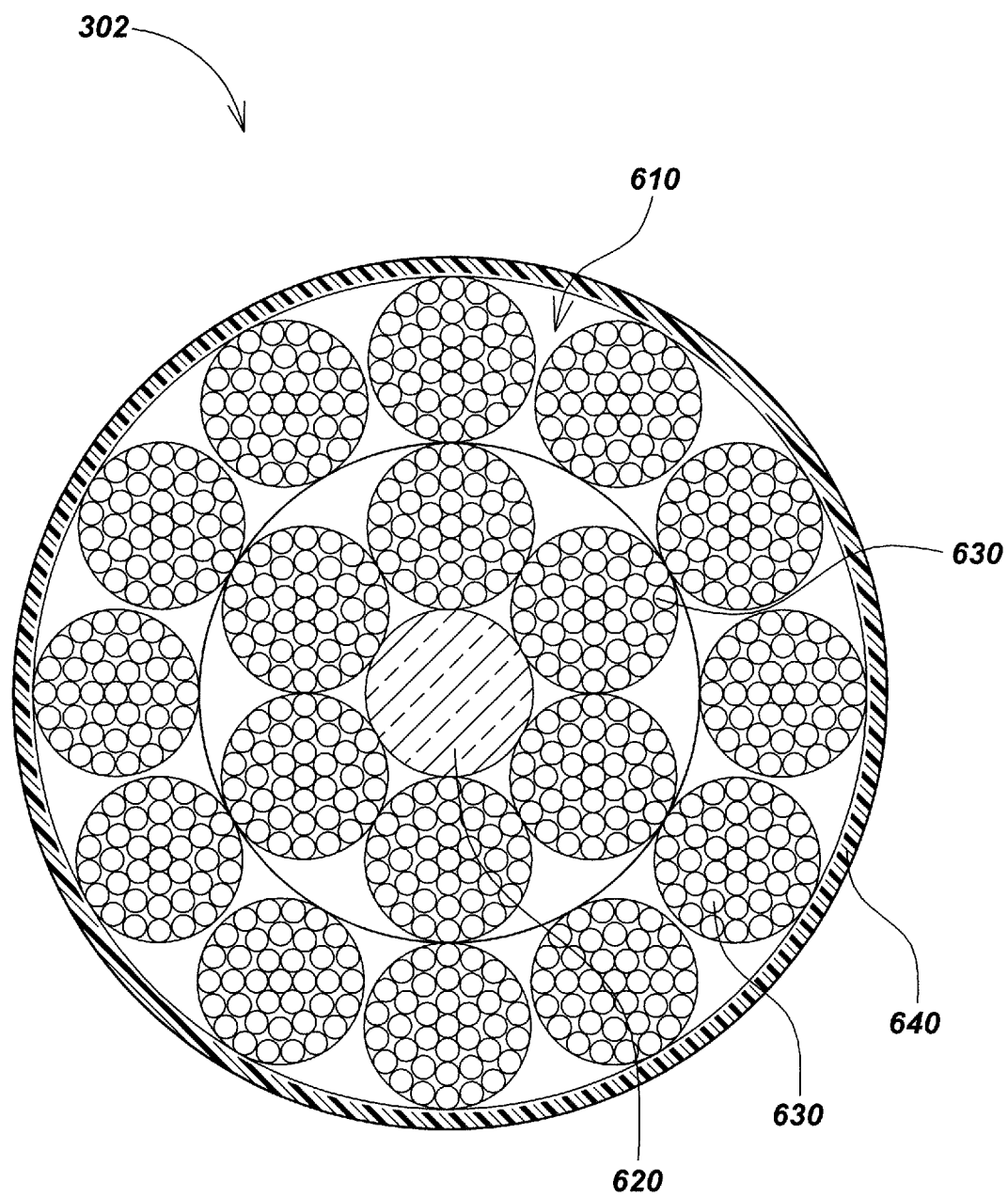
FIG. 6A is a sectional view along lines 6A-6A of the flexible magnetic core embodiment of FIG. 4

FIGS. 6A and 6B illustrate additional details of the flexible magnetic core embodiment 302 of FIG. 3. As shown in FIGS. 6A and 6B, the flexible magnetic core 302 may include a flexible core structure 610 comprising a resiliently deformable rod 620 centrally positioned within a plurality of bundles 630 of high permeability/low loss ferromagnetic wires forming a flexible elongate structure. This configuration may be the same as or similar to the flexible core elements as shown in perspective in FIG. 1.

The central resilient rod 620 may comprise fiberglass, carbon fiber, spring steel or other materials as are described herein or known in the art with similar or equivalent resiliency properties. In some embodiments (not illustrated), multiple central resilient rods may be included to provide a straightening force to the flexible magnetic core to return it to a non-flexed orientation. Each wire bundle 630 may comprise strands of HyMu alloy and/or other similar or equivalent high magnetic permeability/low loss flexible material(s). The strands within each wire bundle 630 may be helically arranged within each wire bundle 630. The plurality of wire bundles 630 may further be helically wound about central resilient rod 620. In other embodiments (not illustrated), alternate numbers/rows of wires and/or wire bundles may be arranged/wound in various patterns in flexible magnetic core embodiments in keeping with the present disclosure. The flexible magnetic core assembly 302 may further include a jacket 640 of a plastic or other material encapsulating the core structure 610 which may be airtight, watertight and/or otherwise provide protection from the external environment alone or in conjunction with additional layers (not shown).

Figure 7:
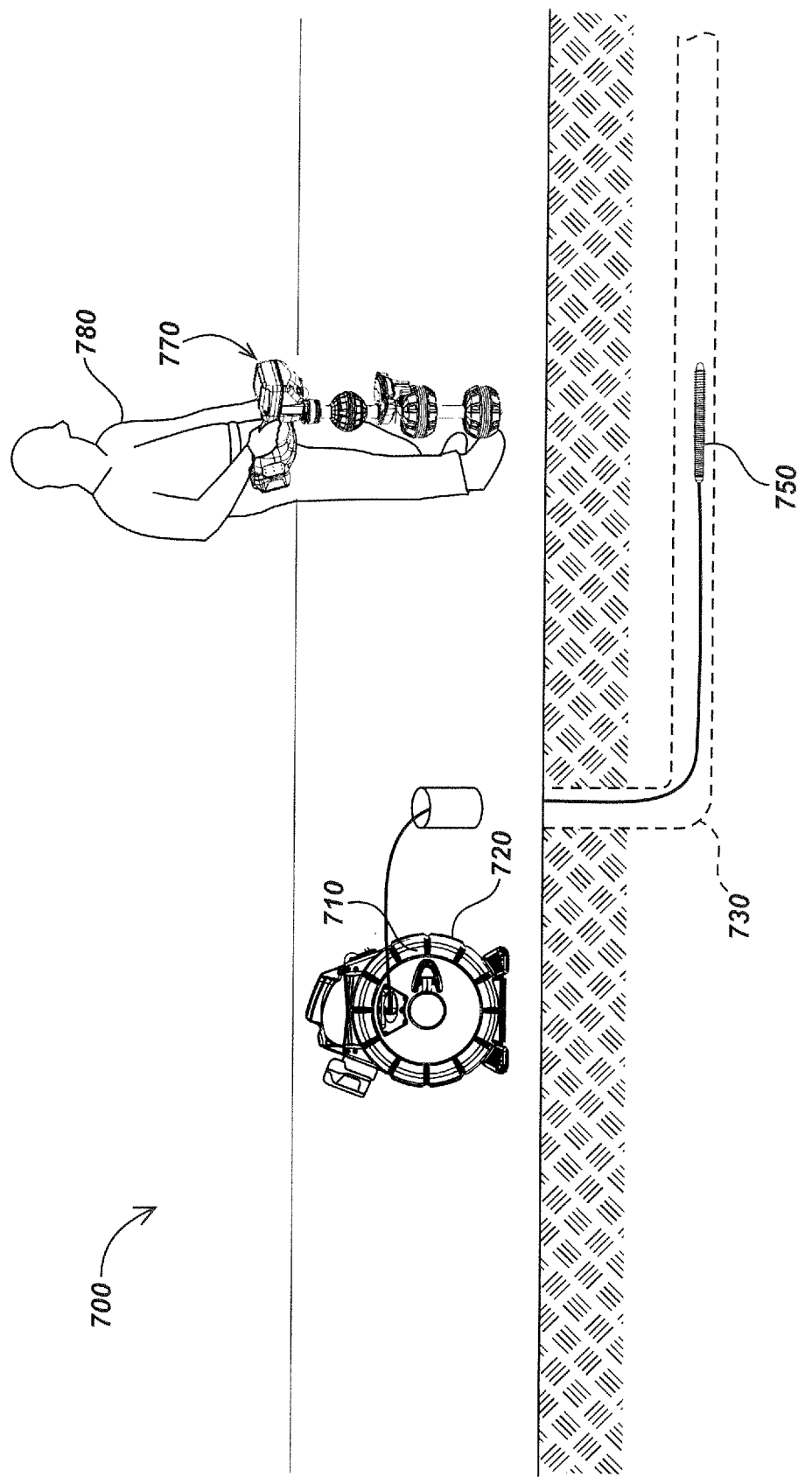
FIG. 7 is an exemplary utility locating system with a duct fishing/tracing sonde embodiment including a flexible magnetic core embodiment.

Turning to FIG. 7, another exemplary embodiment of a utility locating system 700 is illustrated. System 700 illustrates an embodiment of system for locating a line and/or cable disposed within a duct or other such cavity utilizing a duct fishing/tracing sonde embodiment 750 (also denoted here in as a "tracing sonde" for brevity). Tracing sonde 570 may include a flexible magnetic core as disclosed herein.

Locating system 700 may include a push-cable 710 that may be dispensed from a drum reel 720 into a pipe 730. Electrical and mechanical connections may be provided by the push-cable 710 between the drum reel 720 and tracking sonde 750 (which may be disposed on or about a distal-most section of push-cable 710). The push-cable 710 may communicate control signals between the tracing sonde 750 and a drum reel 220, as well as transmit electrical power to the sonde 750 from a power source, such as one or more batteries (not illustrated), on drum reel 720. In some embodiments the batteries may be disposed on or within the tracing sonde 750. A utility locator 770 as held by user 780 may determine, track, and/or map the location of the tracing sonde 750 within pipe 730. Further details of utility locating devices, systems, and methods as may be used in conjunction with the tracking sonde 750 as shown in FIG. 7 are described in the incorporated patents and patent applications.

Figure 8:
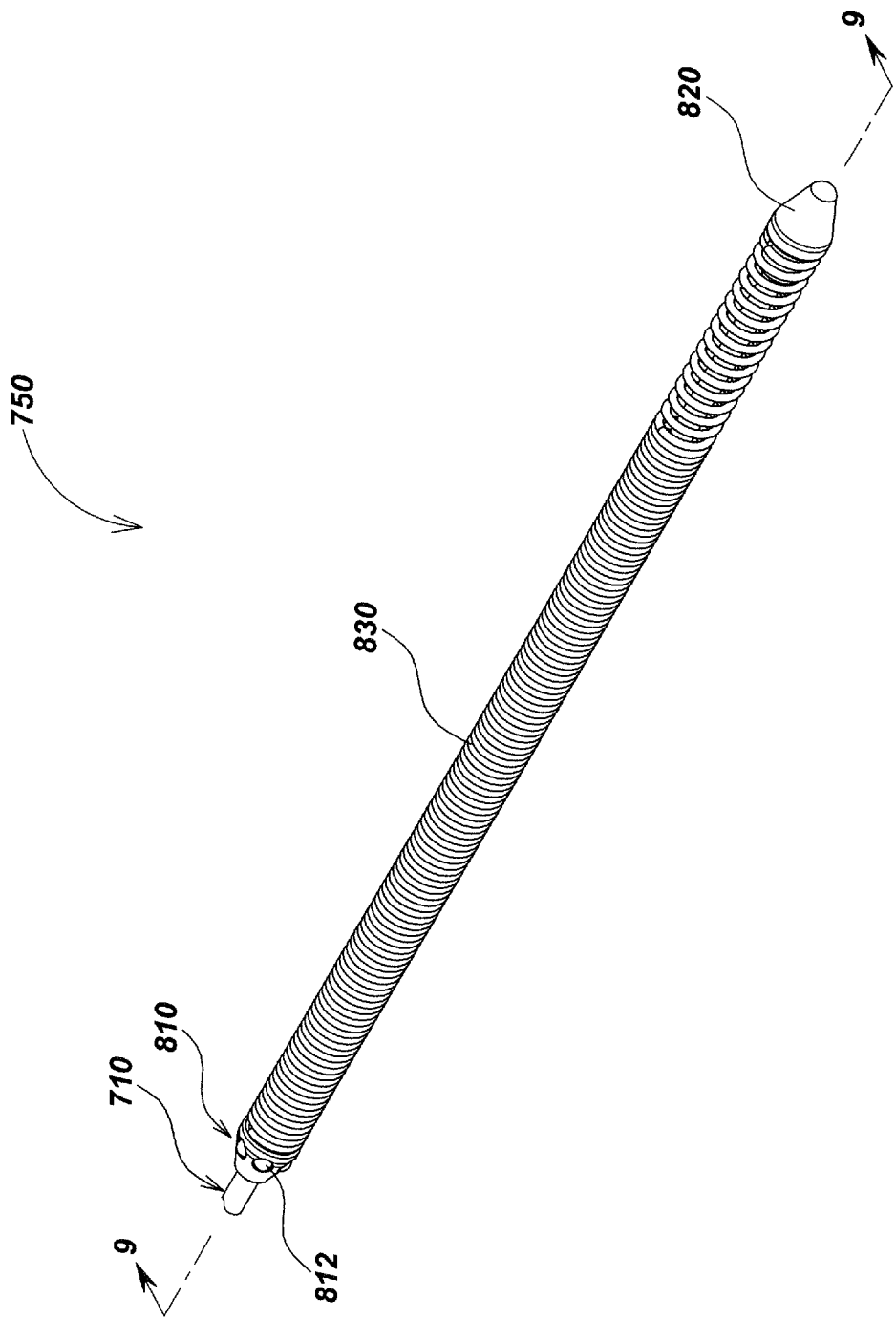
FIG. 8 is an isometric view of the duct fishing/tracing sonde embodiment.

As best illustrated in FIG. 8, the duct fishing/tracing sonde 750 may include a rear terminal 810 (which may allow external connection to a push-cable), a front terminal 820, and an optional coil spring 830. The rear terminal 810 may secure the duct tracing sonde 750 to push-cable 710 and provide an electromechanical connection thereto. For instance, force applied to crimp balls 812 may be used to crimp and secure the rear terminal 810 to the push-cable 710. The front terminal 820 may be shaped to aid the tracing sonde 750 in traverse turns and bends. For instance, the front terminal may be conical or, in some embodiments, hemispherical to prevent the tracing sonde 750 from snagging within the pipe or other cavity. Coil spring 830 may provide additional protection and rigidity as the tracing sonde 750 is pushed through a pipe (such as pipe 730 of FIG. 7) while allowing the sonde to bend and flex to a degree through turns within. The spring 830 may further be used to secure the rear terminal 810 and front terminal 820 together in place. For instance, threads (not illustrated) formed on the rear terminal 810 and front terminal 820 may mate and allow end coils of the coil spring 830 to seat therein.

Figure 9:
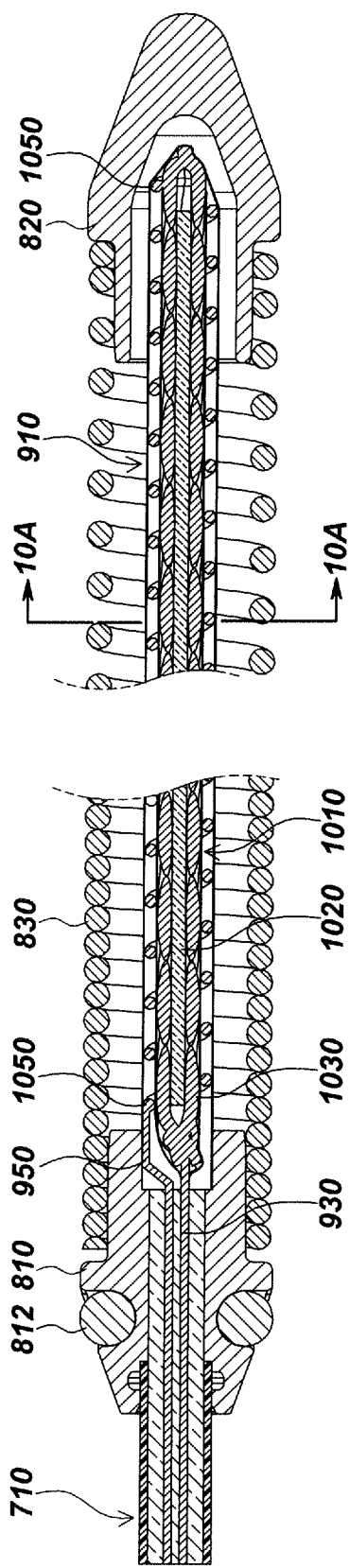
FIG. 9 is a detailed sectional view along lines 9-9 of the duct fishing/tracing sonde embodiment of FIG. 8.

As shown in FIG. 9, a flexible magnetic antenna embodiment 910 may be disposed with the coil spring 830. The flexible magnetic antenna 910 may include a flexible magnetic core as described herein. For example antenna 910 may be seated and secured between the rear terminal 810 and front terminal 820. The flexible magnetic antenna 910 may seat within cavities formed centrally within the rear terminal 810 and front terminal 820 as shown in FIG. 9. O-rings (not illustrated) or other similar elements may be used to provide a watertight seal to the flexible magnetic antenna 910 and/or push-cable 710 attached thereto.

Figure 10A:
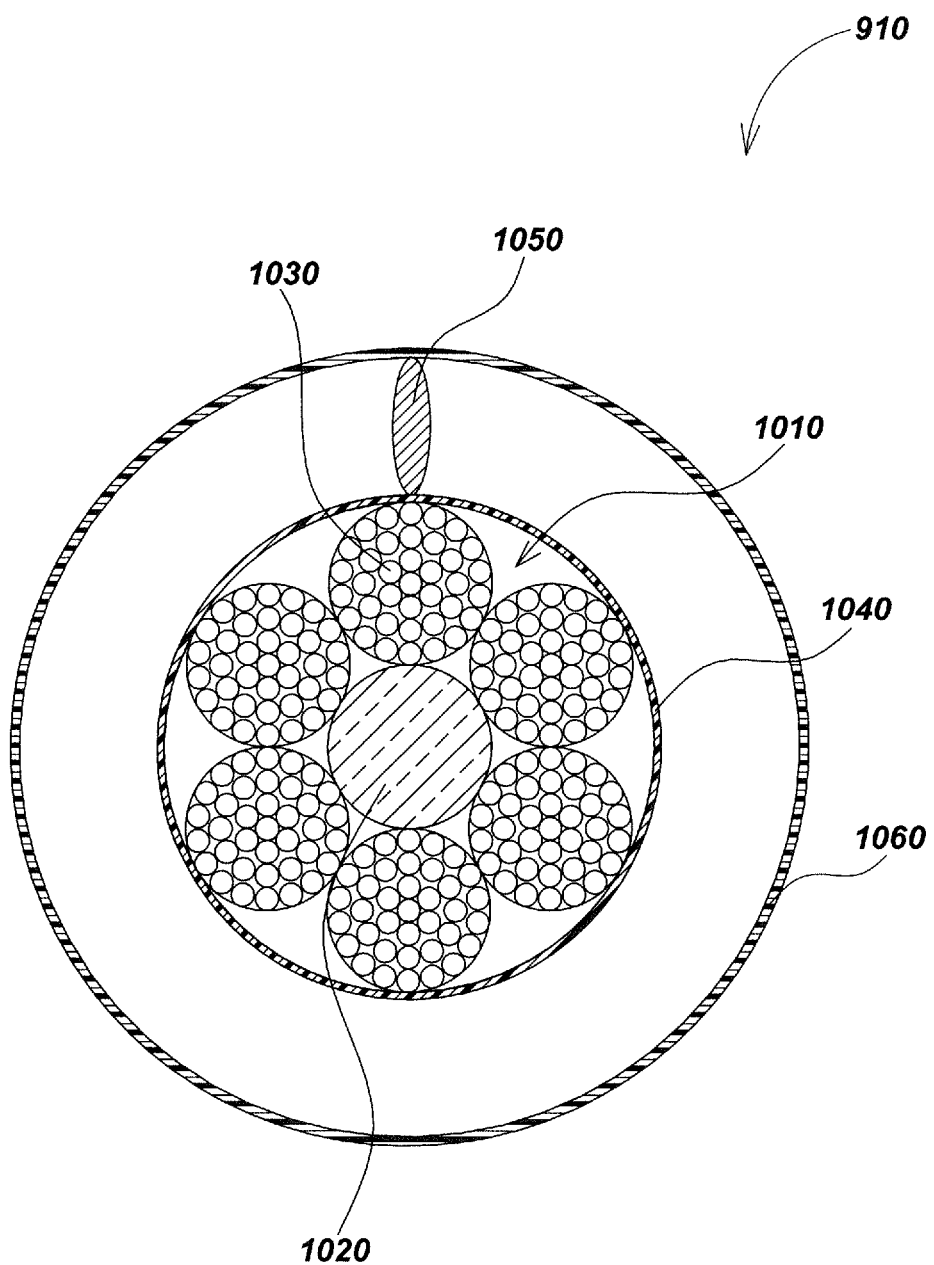
FIG. 10A is a sectional view along lines 10A-10A of the flexible magnetic core embodiment of the sonde embodiment of FIG. 9.
Figure 10B:
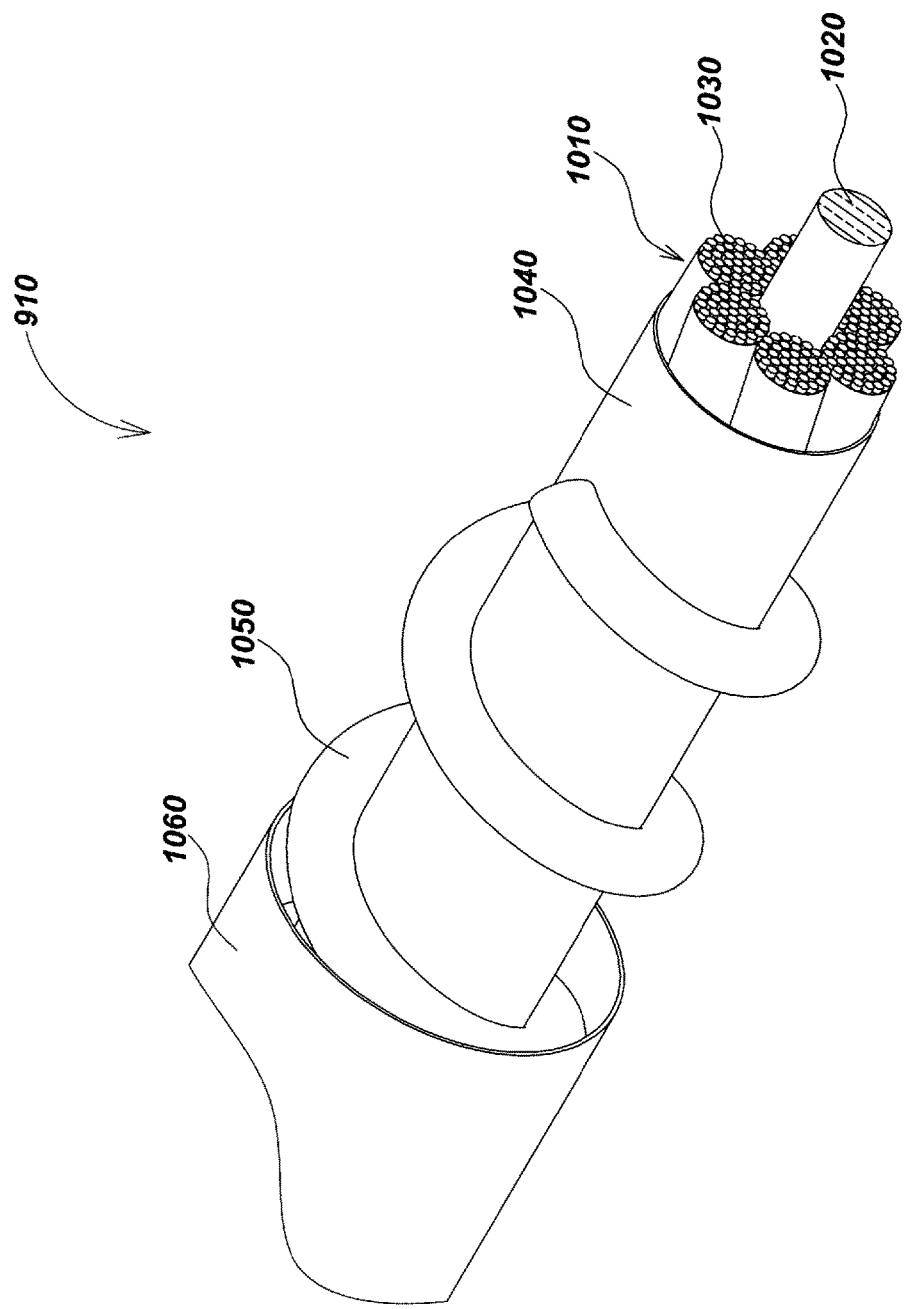
FIG. 10B is a segmented isometric view of the flexible magnetic core embodiment of FIG. 9.

As best illustrated in FIGS. 10A and 10B, the flexible magnetic antenna embodiment 910 of FIG. 9 may include a flexible core 1010 comprising a resiliently deformable rod 1020 that may be centrally positioned within a plurality of wire bundles 1030. Other flexible magnetic core elements and configurations as disclosed herein may alternately be used for the core of antenna embodiment 910.

The resilient rod 1020 may comprise fiberglass, carbon fiber, spring steel or other similar or equivalent materials with similar resiliency properties. In some embodiments (not illustrated), multiple central resilient rods may be included to provide the straightening force to the flexible magnetic antenna, or other elongate flexible elements and/or elongate high permeability material structures may be used.

Each wire bundle 1030 may comprise wires of HyMu alloy and/or other high magnetic permeability/low loss flexible material(s). The strands within each wire bundle 1030 may be helically arranged within each wire bundle 1030. The plurality of wire bundles 1030 may further be helically wound about resilient rod 1020.

In other embodiments (not illustrated), various numbers/rows of wires and/or wire bundles arranged/wound in various shapes or patterns may be used in flexible magnetic antenna embodiment 910. The flexible magnetic antenna 910 may further include an inner jacket 1040 encapsulating the core assembly 1010 which may be airtight, watertight and/or otherwise provide protection from the external environment either alone or with additional layers (not shown). A coil 1050 may be wound helically about the circumference and along the length of the core assembly 1010. An additional outer jacket 1060 may encapsulate the coil wire 1050, inner jacket 1040, and core assembly 1010 which may further be airtight, watertight and/or otherwise provide protection from the external environment.

Turning back to FIG. 9, wire 950 from within push-cable 710 may connect to coil wire 1050 of the flexible magnetic antenna 910 to supply electrical signals. At the distal-end of the flexible magnetic antenna 910, seated within the front terminal 820, the coil wire 1050 may electrically connect to the wire bundles 1030 within the core assembly 1010 of the flexible magnetic antenna 910 to generate magnetic fields when energized. The wire bundles 1030 may provide a return pathway back to wire 930 within push-cable 710.

Figure 11:
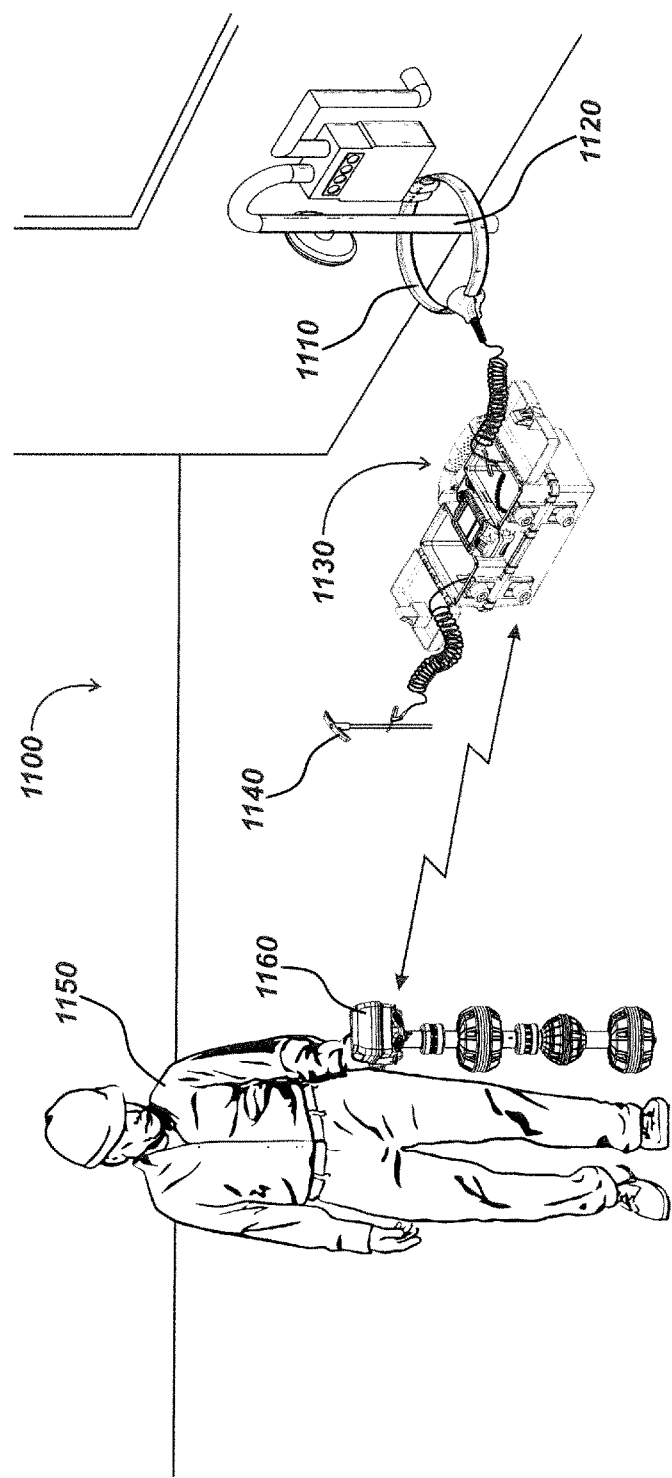
FIG. 11 is an exemplary locating system using a clamp embodiment with a flexible magnetic core embodiment in accordance with certain aspects.
Figure 11:
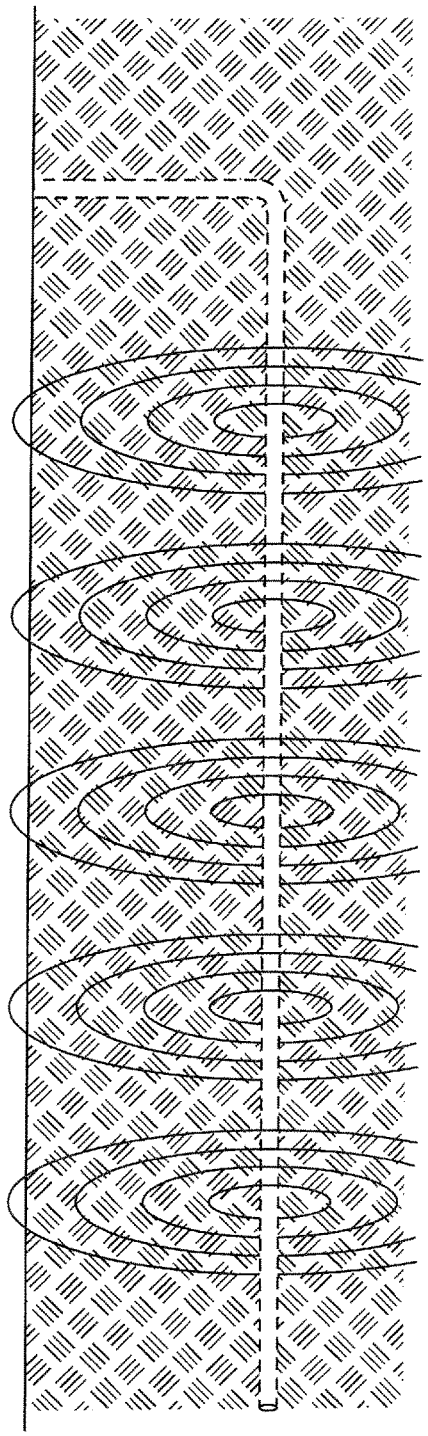

Turning to FIG. 11, the various flexible magnetic core embodiments disclosed herein may be used within an inductive clamp embodiment, such as the clamp device embodiment 1110 illustrated in locating system 1100 of FIG. 11. An inductive clamp is used to induce current flow in a conductor. In a utility locating application the conductor is typically a buried pipe or other conductor.

Clamp embodiment 1110 may be configured to wrap about and induce an electromagnetic signal onto a conductor such as the conductive utility line 1120 when supplied with a current signal. For example, Clamp embodiment 1110 may be electrically connected to a transmitter device 1130 which generates current signals. Magnetic fields generated from the current signals induce current flow onto the utility line 1120 and/or other conductors. A grounding stake 1140 may be connected to the transmitter device 1130 via a cord or cable to provide a ground current flow connection, for example when the transmitter device 1130 is used in a direct connect mode.

A user 1150 equipped with a corresponding utility locator, such as locator 1160 which senses the emitted magnetic field signal(s) associated with current flow in the utility 1120, may then determine information associated with the buried utility 1120, such as depth, position, location, orientation, conductor current, soil condition, presence of other utilities, and the like (example of utility locator devices, systems, and methods of operation are disclosed in various incorporated applications).

Figure 12:
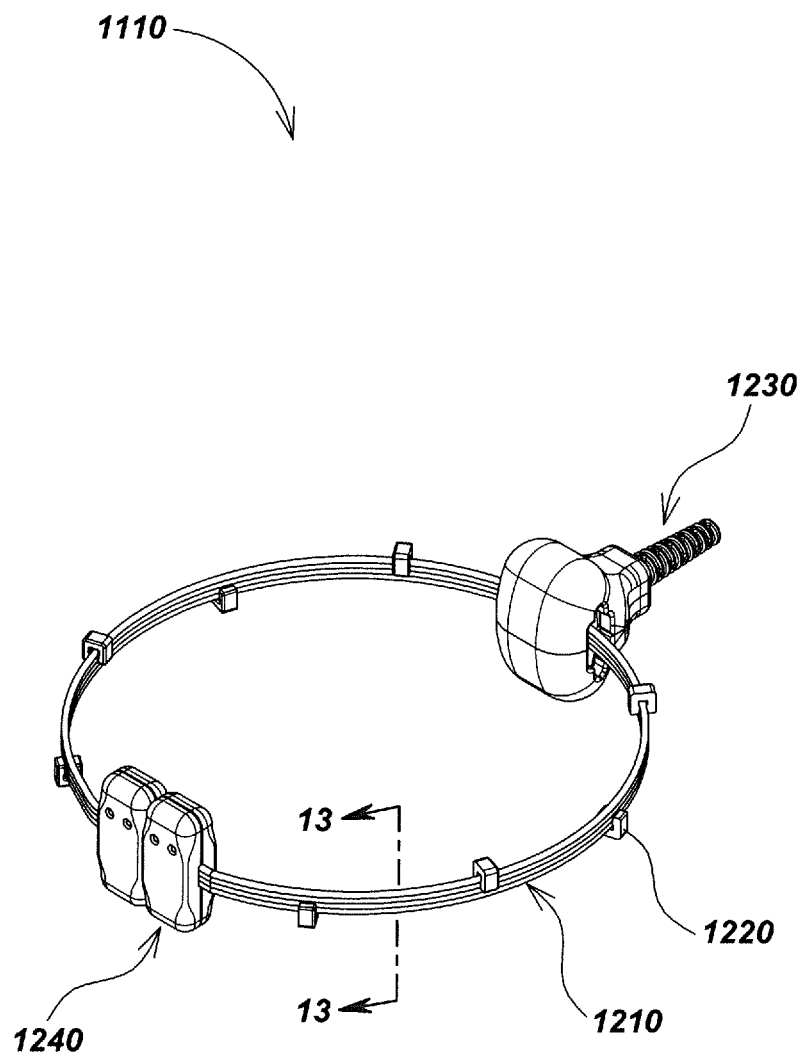
FIG. 12 is a detailed isometric view of the clamp embodiment of FIG. 11.

As illustrated in FIG. 12, the clamp 1110 may be comprised of multiple flexible magnetic cores 1210 (illustrated in more detail in cross-section in FIG. 13) which may be of any of the variety of flexible magnetic core embodiments disclosed herein or their equivalents. In claim 1110, multiple cores are coupled together via retainers 1220, however, they may alternately be mechanically coupled in various ways in different embodiments. The clamp 1110 may further comprise a coil connector and assembly 1230 that may connect the clamp 1110, via cord or cable, to a transmitter such as the utility locator transmitter 1130 of FIG. 11. Additionally, the clamp 1110 may include clasp assemblies 1240 configured such that each clasp assembly 1240 secures to the other clasp assembly 1240 when the clamp device 1110 is closed. The clasp assemblies 1240 may utilize magnets (not illustrated) and/or other mechanical locking mechanisms (not illustrated) to secure together when the clamp device 1110 is closed.

The coil and connector assembly 1230 may, for instance, include a coil of wire disposed upon a bobbin (not illustrated) similar to the coil 520 and bobbin 530 of FIG. 5. The coil of wire may encircle a segment of the flexible magnetic core assemblies 1210 and be configured to induce the flexible magnetic core assemblies 1210 to emit electromagnetic signal(s) at a predetermined frequency which may further be induced onto a conductor such as the utility 1120 illustrated in FIG. 11.

Figure 13:
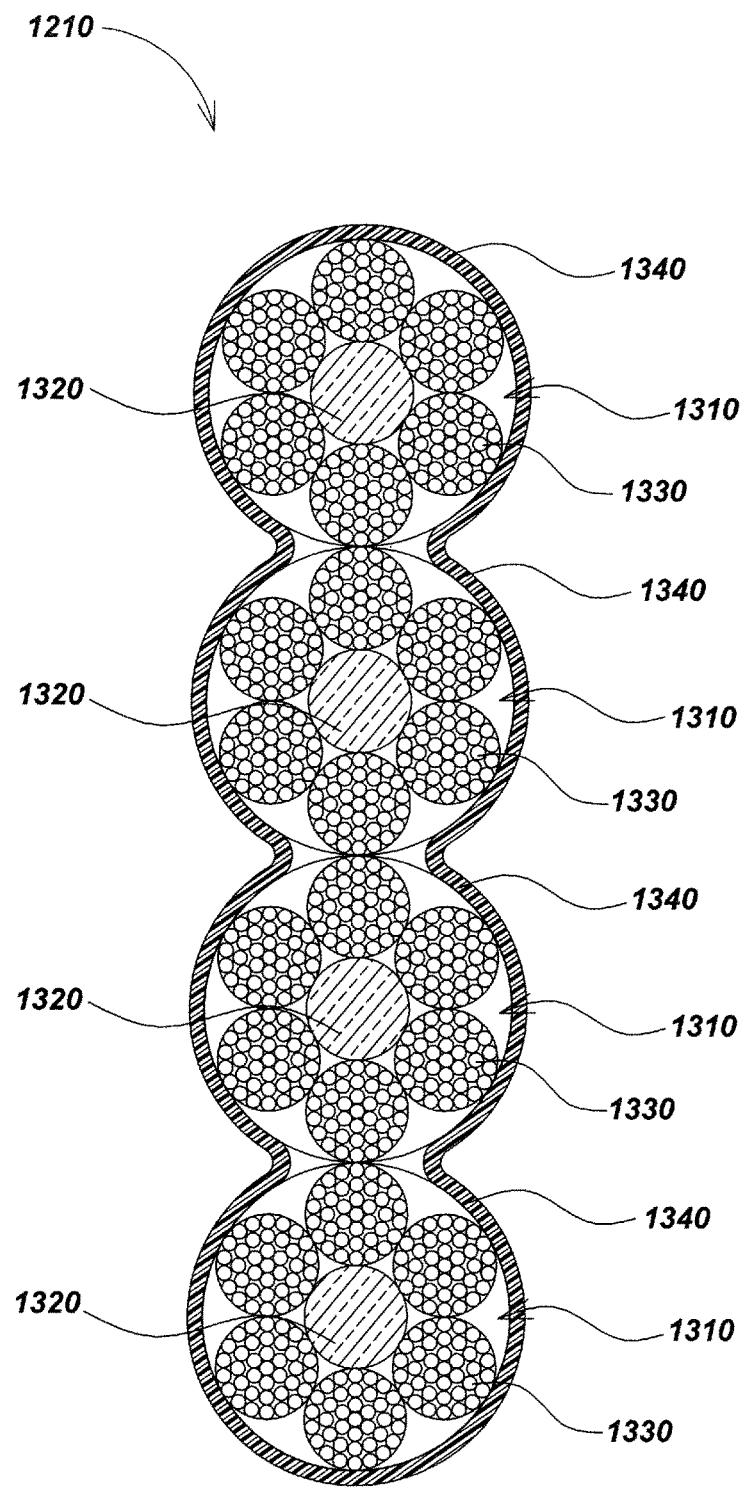
FIG. 13 is a sectional view along lines 13-13 of the flexible magnetic core embodiment of the clamp embodiment of FIG. 12.

As illustrated in FIG. 13, the flexible magnetic core assemblies 1210 may each include a core subassembly 1310 comprising a resiliently deformable rod 1320 that may be centrally disposed within a plurality of wire bundles 1330. The resilient rod 1320 may comprise fiberglass, carbon fiber, spring steel or other materials with similar resiliency properties. In some embodiments (not illustrated), multiple resilient rods may be included to provide the straightening force to the flexible magnetic antenna. The wire bundles 1330 may comprise strands of HyMu alloy and/or other high magnetic permeability/low loss flexible material(s) such as are described herein. The strands within each wire bundle 1330 may be helically arranged within each wire bundle 1330. The collective wire bundles 1330 may further be helically wound about central resilient rod 1320.

In other embodiments (not illustrated), various number/rows of wires and/or wire bundles may be arranged/wound in various patterns in flexible magnetic cores of a clamp embodiment such as clamp 1110. Each of the flexible magnetic cores 1210 may further include a jacket 1340 encapsulating the core subassembly 1310 which may be watertight and/or otherwise provide protection from the external environment.

Other combinations of the various aspects, elements, components, features, and/or functions described previously herein may be used in alternate embodiments. In addition, details regarding additional aspects, elements, components, features, functions, apparatus, and/or methods which may be used in further embodiments in conjunction with the disclosures herein are described in the incorporated applications.

Those of skill in the art would understand that information and signals, such as analog or video signals, data signals, audio signals, or other information signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The scope of the presently claimed invention is not intended to be limited to the aspects shown and described previously herein, but should be accorded the full scope consistent with the language of the claims, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c.

The previous description of the disclosed aspects is provided to enable any person skilled in the art to make or use embodiments of the invention. Various modifications to these aspects will be readily apparent to those skilled in the art, and the generic principles defined herein may be applied to other aspects without departing from the spirit or scope of the invention. Thus, the presently claimed invention is not intended to be limited to the aspects shown herein, but is to be accorded the widest scope consistent with the appended claims and their equivalents.

I claim:

1. A magnetic field sonde for use in pipe inspection, comprising:
   a waterproof housing having an electronics assembly disposed in the housing and operatively coupled to a power supply for generating an output current signal;
   a flexible magnetic core including:
   an elongate resiliently deformable rod; and
   a flexible elongate structure disposed around the elongate resiliently deformable rod;
   a coil operatively coupled to the output current signal and wound on the flexible magnetic core;
   a rear connector to operatively couple the sonde to a push-cable; and
   a front connector to operatively couple the sonde to a pipe inspection camera head.

2. The sonde of claim 1, wherein the flexible elongate structure includes:
   one or more elongate wire bundles each including a plurality of elongate wires of a ferromagnetic material having permeability of about 5,000 Mu or higher; and
   a protective jacket encapsulating and protecting the magnetic core from an external environment.

3. The sonde of claim 1, wherein the elongate resiliently deformable rod is positioned in the center of the flexible magnetic core.

4. The sonde of claim 1, further comprising one or more additional elongate resiliently deformable rods.

5. The sonde of claim 1, wherein the elongate resiliently deformable rod comprises fiberglass or carbon fiber.

6. The sonde of claim 1, wherein the elongate resiliently deformable rod comprises a polymer material.

7. The sonde of claim 1, wherein the elongate resiliently deformable rod comprises a metallic material comprising a spring steel alloy.

8. The sonde of claim 1, wherein the elongate resiliently deformable rod comprises a material having a tensile strength of approximately 1,000 MPa or more.

9. The sonde of claim 1, wherein the ferromagnetic material comprises an alloy.

10. The sonde of claim 9, wherein the alloy comprises a nickel nickel-iron-molybdenum alloy.

11. The sonde of claim 1, wherein the ferromagnetic material comprises a metallic glass (Metglas) material.

12. The sonde of claim 1, wherein the ferromagnetic material has a permeability of approximately 8,000 Mu or more.

13. The sonde of claim 2, wherein the plurality of elongate wires are axially positioned within the one or more elongate wire bundles.

14. The sonde of claim 2, wherein the plurality of elongate wires are helically wound within the one or more elongate wire bundles.

15. The sonde of claim 2, wherein the one or more elongate wire bundles comprises a plurality of elongate wire bundles.

16. The sonde of claim 15, wherein the plurality of elongate wire bundles are helically wound with the core.

17. The sonde of claim 15, wherein the plurality of elongate wire bundles are helically wound about the elongate resiliently deformable rod.

18. The sonde of claim 1, wherein the elongate resiliently deformable rod is positioned in approximately the center of the core and the plurality of elongate wire bundles are positioned longitudinally about the elongate resiliently deformable rod.

19. The sonde of claim 1, wherein the magnetic core comprises a core assembly including a plurality of elongate resiliently deformable rods, and wherein ones of the plurality of wire bundles are interspersed with ones of the plurality of elongate resiliently deformable rods.

20. The sonde of claim 19, wherein the plurality of wire bundles are helically wound within the core assembly.

21. The sonde of claim 1, further comprising a jacket enclosing the elongate resiliently deformable rod and the flexible elongate structure.

* * * * *